US011744288B2

(12) United States Patent
Blackmon et al.

(10) Patent No.: US 11,744,288 B2
(45) Date of Patent: Sep. 5, 2023

(54) CAPSULES INCLUDING INTERNAL FILTERS, HEAT-NOT-BURN (HNB) AEROSOL-GENERATING DEVICES, AND METHODS OF GENERATING AN AEROSOL

(71) Applicant: Altria Client Services LLC, Richmond, VA (US)

(72) Inventors: Zack W. Blackmon, Williamsburg, VA (US); Patrick Good, Richmond, VA (US); Rangaraj S. Sundar, Midlothian, VA (US); Jarrett Keen, Richmond, VA (US); Eric Hawes, Midlothian, VA (US); Yannick Hourmand, Haslingfield (GB); Niall Gallagher, Cambridge (GB)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 336 days.

(21) Appl. No.: 16/916,607

(22) Filed: Jun. 30, 2020

(65) Prior Publication Data

US 2021/0401042 A1 Dec. 30, 2021

(51) Int. Cl.
*A24F 47/00* (2020.01)
*A24F 40/42* (2020.01)
(Continued)

(52) U.S. Cl.
CPC ............ *A24F 40/42* (2020.01); *A24D 3/17* (2020.01); *A24F 7/00* (2013.01); *A24F 40/20* (2020.01);
(Continued)

(58) Field of Classification Search
None
See application file for complete search history.

(56) References Cited

U.S. PATENT DOCUMENTS 9,693,587 B2 7/2017 Plojoux et al.
10,172,390 B2 1/2019 Nakano et al.
(Continued)

FOREIGN PATENT DOCUMENTS

CN 206025226 U 3/2017
EP 3338571 A2 6/2018
(Continued)

OTHER PUBLICATIONS

CA International Search Report and Written Opinion for PCT/US2021/021302 dated Jun. 7, 2021.
(Continued)

*Primary Examiner* — Eric Yaary
(74) *Attorney, Agent, or Firm* — Harness, Dickey & Pierce, P.L.C.

(57) ABSTRACT

A capsule for an aerosol-generating device may include a housing, a filter, and an aerosol-forming substrate. The housing may have a gas-permeable end and an impermeable end. The filter may be disposed within the housing so as to be adjacent to the impermeable end. The aerosol-forming substrate may be disposed within the housing so as to be between the filter and the gas-permeable end. The housing may be configured to facilitate a heating of the aerosol-forming substrate via one of conduction, convection, or both conduction and convection so as to generate an aerosol.

19 Claims, 10 Drawing Sheets

(51) Int. Cl.
*A61M 15/00* (2006.01)
*A24F 40/485* (2020.01)
*A24F 40/46* (2020.01)
*A24F 40/20* (2020.01)
*A24D 3/17* (2020.01)
*A24F 7/00* (2006.01)

(52) U.S. Cl.
CPC ............ *A24F 40/46* (2020.01); *A24F 40/485* (2020.01); *A61M 15/003* (2014.02); *A61M 15/009* (2013.01); *A61M 15/0021* (2014.02); *A61M 15/0025* (2014.02); *A61M 2205/36* (2013.01); *A61M 2205/75* (2013.01)

(56) References Cited

U.S. PATENT DOCUMENTS

| | | | |
|---|---|---|---|
| 10,292,436 | B2 | 5/2019 | Cirillo et al. |
| 10,328,443 | B2 | 6/2019 | Ricketts et al. |
| 2010/0065075 | A1* | 3/2010 | Banerjee ............... A24B 15/288 131/334 |
| 2013/0255702 | A1 | 10/2013 | Griffith, Jr. et al. |
| 2018/0007960 | A1 | 1/2018 | Suzuki et al. |
| 2018/0007961 | A1 | 1/2018 | Zhu |
| 2019/0006866 | A1 | 1/2019 | Zhu |
| 2020/0008475 | A1 | 1/2020 | Lai et al. |
| 2022/0183348 | A1* | 6/2022 | Selby ....................... A24D 1/20 |

FOREIGN PATENT DOCUMENTS

| | | |
|---|---|---|
| EP | 3469927 A1 | 4/2019 |
| EP | 3656231 A1 | 5/2020 |

OTHER PUBLICATIONS

International Preliminary Report on Patentability dated Jan. 12, 2023 issued in related international patent application No. PCT/US2021/021302.

* cited by examiner

CAPSULES INCLUDING INTERNAL FILTERS, HEAT-NOT-BURN (HNB) AEROSOL-GENERATING DEVICES, AND METHODS OF GENERATING AN AEROSOL

BACKGROUND

Field

The present disclosure relates to capsules, heat-not-burn (HNB) aerosol-generating devices, and methods of generating an aerosol without involving a substantial pyrolysis of the aerosol-forming substrate.

Description of Related Art

Some electronic devices are configured to heat a plant material to a temperature that is sufficient to release constituents of the plant material while keeping the temperature below a combustion point of the plant material so as to avoid any substantial pyrolysis of the plant material. Such devices may be referred to as aerosol-generating devices (e.g., heat-not-burn aerosol-generating devices), and the plant material heated may be tobacco. In some instances, the plant material may be introduced directly into a heating chamber of an aerosol-generating device. In other instances, the plant material may be pre-packaged in individual containers to facilitate insertion and removal from an aerosol-generating device.

SUMMARY

At least one embodiment relates to a capsule for a heat-not-burn (HNB) aerosol-generating device. In an example embodiment, the capsule may include a housing, a filter, and an aerosol-forming substrate. The housing may have a gas-permeable end and an impermeable end. The filter may be disposed within the housing so as to be adjacent to the impermeable end. The aerosol-forming substrate may be disposed within the housing so as to be between the filter and the gas-permeable end. The housing may be configured to facilitate a heating of the aerosol-forming substrate via one of conduction, convection, or both conduction and convection so as to generate an aerosol.

At least one embodiment relates to a heat-not-burn (HNB) aerosol-generating device. In an example embodiment, the aerosol-generating device may include a device body, a mouthpiece, and a heating assembly. The device body may define a compartment configured to receive a capsule containing an aerosol-forming substrate and a filter. The mouthpiece may include a conduit portion. The mouthpiece may be configured to engage with the device body such that the conduit portion extends through the aerosol-forming substrate and into the filter of the capsule. The heating assembly may be disposed within the device body. The heating assembly may be configured to heat the aerosol-forming substrate within the capsule via one of conduction, convection, or both conduction and convection so as to generate an aerosol that exits the capsule via the conduit portion of the mouthpiece.

At least one embodiment relates to a method of generating an aerosol. In an example embodiment, the method may include heating a capsule including a housing, a filter, and an aerosol-forming substrate. The housing may have a gas-permeable end and an impermeable end. The method may additionally include directing a drawn flow of air along a meandering path through the capsule. The meandering path may include an entrained flow section and a filtered flow section. The entrained flow section may be from the gas-permeable end of the housing through the aerosol-forming substrate to the filter. The filtered flow section may be from the filter to the gas-permeable end of the housing.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

Figure 1:
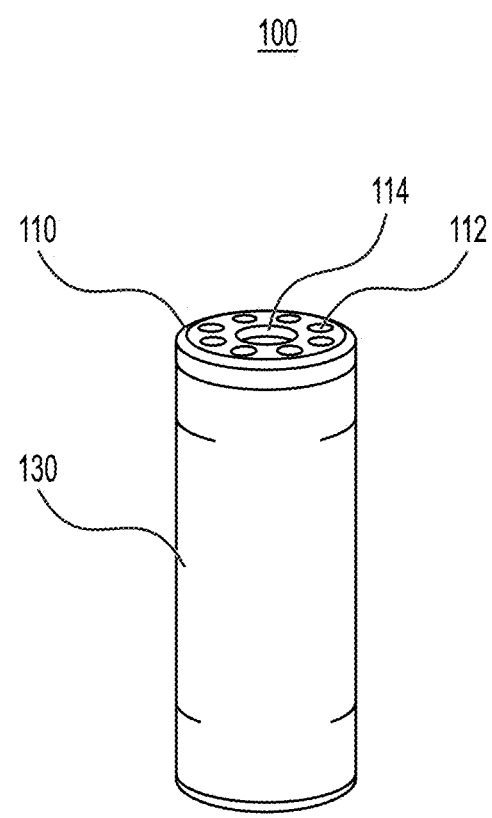
FIG. 1 is a first perspective view of a capsule for an aerosol-generating device according to an example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives thereof. Like numbers refer to like elements throughout the description of the figures.

It should be understood that when an element or layer is referred to as being "on," "connected to," "coupled to," "attached to," "adjacent to," or "covering" another element or layer, it may be directly on, connected to, coupled to, attached to, adjacent to or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/ or" includes any and all combinations or sub-combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, and/or elements, but do not preclude the presence or addition of one or more other features, integers, steps, operations, elements, and/or groups thereof.

When the terms "about" or "substantially" are used in this specification in connection with a numerical value, it is intended that the associated numerical value includes a manufacturing or operational tolerance (e.g., ±10%) around the stated numerical value. Moreover, when the terms "generally" or "substantially" are used in connection with geometric shapes, it is intended that precision of the geometric shape is not required but that latitude for the shape is within the scope of the disclosure. Furthermore, regardless of whether numerical values or shapes are modified as "about," "generally," or "substantially," it will be understood that these values and shapes should be construed as including a manufacturing or operational tolerance (e.g., ±10%) around the stated numerical values or shapes.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Hardware may be implemented using processing or control circuitry such as, but not limited to, one or more processors, one or more Central Processing Units (CPUs), one or more microcontrollers, one or more arithmetic logic units (ALUs), one or more digital signal processors (DSPs), one or more microcomputers, one or more field programmable gate arrays (FPGAs), one or more System-on-Chips (SoCs), one or more programmable logic units (PLUs), one or more microprocessors, one or more Application Specific Integrated Circuits (ASICs), or any other device or devices capable of responding to and executing instructions in a defined manner.

Figure 2:
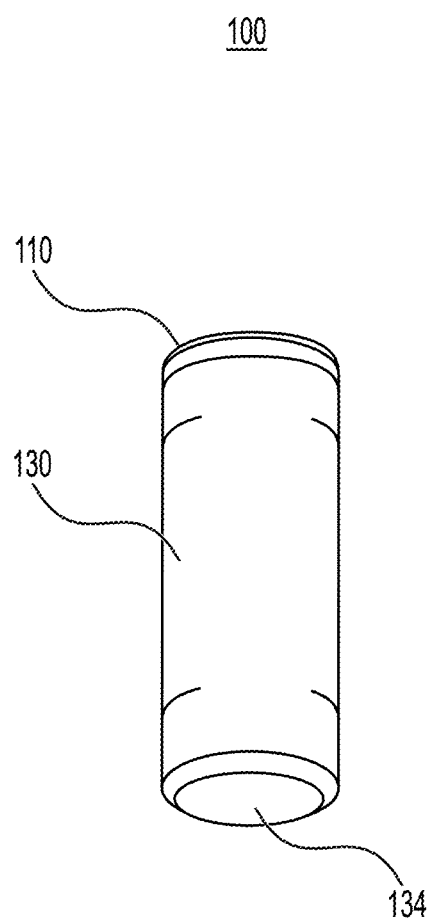
FIG. 2 is a second perspective view of the capsule of FIG. 1.

FIG. 1 is a first perspective view of a capsule for an aerosol-generating device according to an example embodiment. FIG. 2 is a second perspective view of the capsule of FIG. 1. Referring to FIGS. 1-2, the capsule 100 may be configured to be received within an aerosol-generating device (e.g., heat-not-burn aerosol-generating device). The capsule 100 includes a housing configured to hold an aerosol-forming substrate and to facilitate a heating of the aerosol-forming substrate via conduction and/or convection so as to generate an aerosol.

As illustrated, the capsule 100 may have a form resembling a cylinder. With such a form, the capsule 100 may have a circular cross-section. However, it should be understood that other forms and shapes are also possible. For instance, the capsule 100 may, in the alternative, have a form resembling a triangular prism, a cuboid, a pentagonal prism, or a hexagonal prism. With a form resembling a triangular prism, the capsule 100 may have a triangular cross-section (e.g., shape of an equilateral triangle). With a form resembling a cuboid, the capsule 100 may have a square cross-section or a rectangular cross-section. With a form resembling a pentagonal prism, the capsule 100 may have a pentagonal cross-section. With a form resembling a hexagonal prism, the capsule 100 may have a hexagonal cross-section.

The housing of the capsule 100 has a gas-permeable end and an impermeable end. As will be discussed in more detail herein, the gas-permeable end of the housing is configured to retain the aerosol-forming substrate while allowing air to enter the capsule and the aerosol to exit the capsule. A filter 120 (FIG. 3) may be disposed within the housing so as to be adjacent to the impermeable end. Additionally, the aerosol-forming substrate is disposed within the housing so as to be between the filter 120 and the gas-permeable end.

Figure 3:
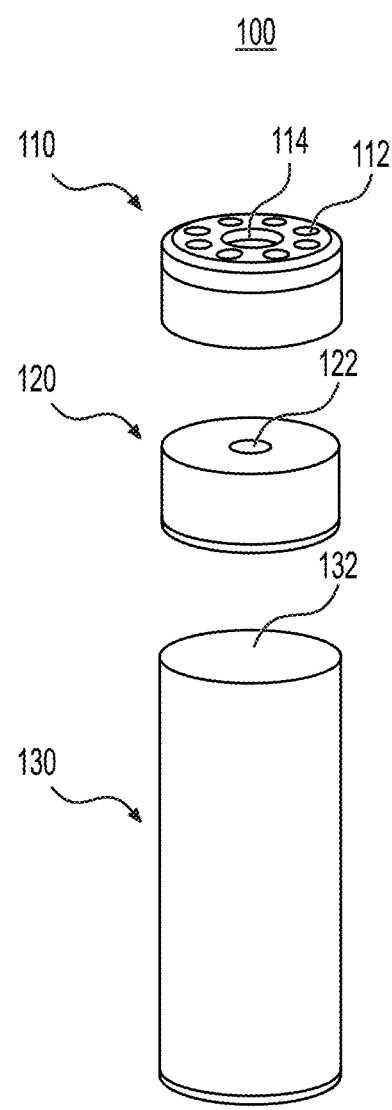
FIG. 3 is an exploded view of the capsule of FIG. 1.

In an example embodiment, the housing of the capsule 100 includes a container 130 and an end cap 110. The container 130 has a closed end 134 and an open end 132 (FIG. 3). The closed end 134 of the container 130 may have rounded edges. However, it should be understood that other configurations are also possible (e.g., beveled edges). The container 130 is made of a conductive material. For instance, the conductive material may be a metal, and the metal may include aluminum, an alloy thereof, or stainless steel. As a result, the container 130 may facilitate a heating of the aerosol-forming substrate within via at least conduction.

During assembly, the end cap 110 is disposed at the open end 132 of the container 130 so as to enclose the aerosol-forming substrate and the filter 120 therein. For instance, a majority of the end cap 110 may be inserted within the container 130. The engagement between the end cap 110 and the container 130 may be via an interference fit (which may also be referred to as a press fit or friction fit). Furthermore, in lieu of or in addition to the interference fit, the end cap 110 may also be secured to the container 130 with an adhesive (e.g., glue) that has been deemed food-safe or otherwise acceptable by a regulatory authority. The end cap 110 may be formed of a suitable plastic (e.g., via molding), although example embodiments are not limited thereto.

The end cap 110 of the capsule 100 defines a plurality of openings. In this regard, the end cap 110 may be regarded as the gas-permeable end of the housing, and the closed end 134 of the container 130 may be regarded as the impermeable end. As illustrated, the plurality of openings in the end cap 110 includes an outlet opening 114 surrounded by inlet openings 112. While eight inlet openings 112 are shown in FIG. 1, it should be understood that a different quantity may be implemented (e.g., six inlet openings, ten inlet openings) based on various factors that may affect the air flow within the capsule 100 (e.g., density of the aerosol-forming substrate, permeability of the filter 120). In an example embodiment, the quantity and size of the inlet openings 112 may be designed to yield a desired resistance to draw (RTD), such as an RTD between 90-110 mm Hg, for the capsule 100.

The inlet openings 112 in the end cap 110 may be equidistant from each other by a first distance. Stated differently, each of the inlet openings 112 may be equidistant from an adjacent inlet opening 112 by a first distance. Additionally, the inlet openings 112 may be equidistant from the center (e.g., diametric center) of the end cap 110 by a second distance. The first distance may be less than the second distance, although example embodiments are not limited thereto. For instance, if the quantity of the inlet openings 112 were decreased, then the first distance may be greater than the second distance. During the operation of the aerosol-generating device, air enters the capsule 100 via the inlet openings 112, and aerosol exits the capsule 100 via the outlet opening 114 (e.g., as a result of an engagement with a mouthpiece, such as mouthpiece 310 in FIG. 5). Each of the inlet openings 112 may be smaller than the outlet opening 114.

Figure 4:
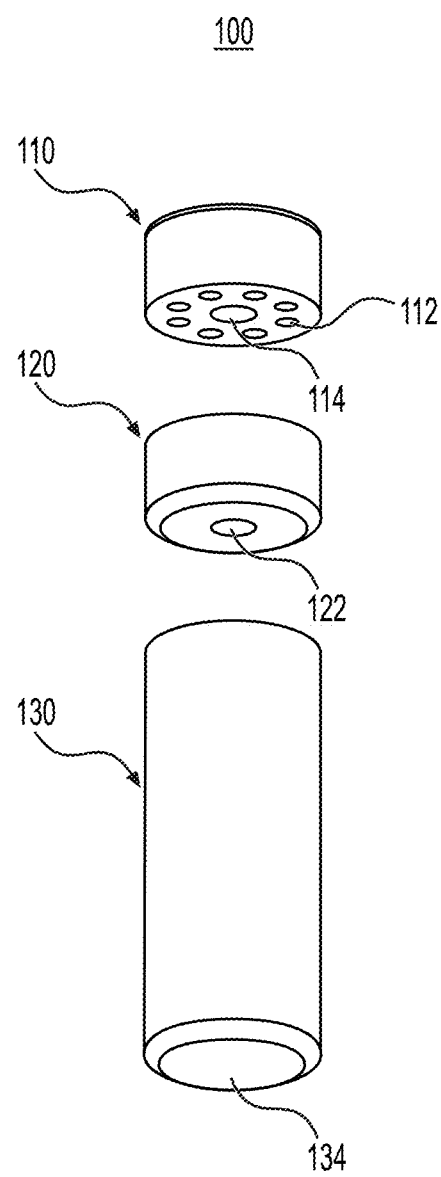
FIG. 4 is an exploded view of the capsule of FIG. 2.

FIG. 3 is an exploded view of the capsule of FIG. 1. FIG. 4 is an exploded view of the capsule of FIG. 2. Referring to FIGS. 3-4, the filter 120 is configured to be inserted into the container 130 via the open end 132 during the assembly of the capsule 100. When fully seated within the container 130, the filter 120 is configured to be adjacent to or pressed against the inner end surface corresponding to the closed end 134. To facilitate the seating within the container 130, the bottom of the filter 120 may be shaped (e.g., provided with rounded edges) so as to conform to the inner surfaces corresponding to the closed end 134. The filter 120 may additionally be sized such that its outer sidewall interfaces with the inner sidewall of the container 130 so as to result in a close-fit arrangement. In such an instance, the filter 120 may sufficiently grip the inner sidewall of the container 130 so as to be able to maintain its seated position (e.g., sufficient to overcome gravity in the event the container 130 is turned upside down).

The filter 120 defines an orifice 122 configured to be aligned with the outlet opening 114 in the end cap 110 when the capsule 100 is assembled. In an example embodiment, the orifice 122 in the filter 120 may be the same or substantially the same size as the outlet opening 114 in the end cap 110. Additionally, the orifice 122 in the filter 120 may be a central through hole. However, in another instance, the orifice 122 in the filter 120 may be a central blind hole.

The filter 120 may be formed of a fibrous material or a foam material. In one instance, the fibrous material for the filter 120 may include cellulose acetate fibers. In another instance, the foam material may include an open-cell foam. Additionally, the filter 120 may include additives configured to modify the aerosol generated within the capsule 100. For instance, the additives may include activated carbon and/or flavorants embedded within the filter 120. In an example embodiment, the filter 120 may include a cigarette filter material as known in the art.

Figure 5:
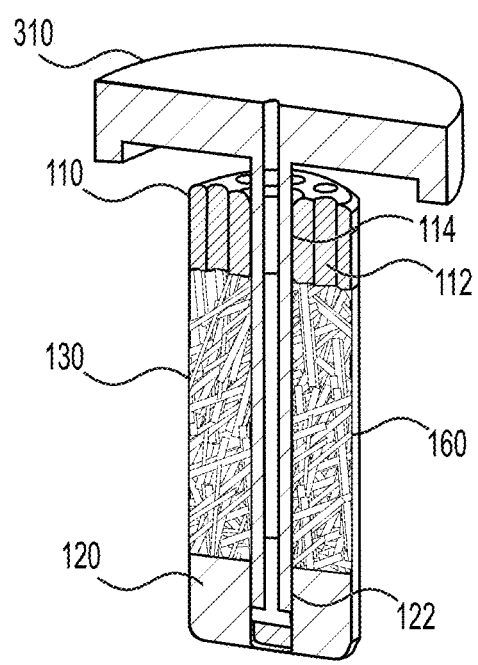
FIG. 5 is a cross-sectional view of the capsule of FIG. 1 when engaged with a mouthpiece.

FIG. 5 is a cross-sectional view of the capsule of FIG. 1 when engaged with a mouthpiece. Referring to FIG. 5, the capsule 100 includes a chamber configured to receive the aerosol-forming substrate 160. As illustrated, the chamber may be defined by the inner sidewall of the container 130 and the opposing inner surfaces of the filter 120 and the end cap 110. In an example embodiment, the outlet opening 114 in the end cap 110 coincides with a central longitudinal axis of the container 130. Additionally, as noted supra, the orifice 122 in the filter 120 may be aligned with the outlet opening 114 in the end cap 110 when the capsule 100 is assembled. As a result, in such an instance, the orifice 122 in the filter 120 may also coincide with the central longitudinal axis of the container 130. As will be discussed in more detail herein, the filter 120 and the aerosol-forming substrate 160 are disposed within the housing such that, during aerosol generation, the air entering the capsule 100 via the inlet openings 112 in the end cap 110 passes through the aerosol-forming substrate 160 in the chamber before reaching the filter 120. Furthermore, the aerosol generated in the chamber passes through the filter 120 before exiting the capsule 100 via the outlet opening 114 in the end cap 110 as a result of an engagement with a mouthpiece 310. The orifice 122 in the filter 120 may be configured such that a passage of the aerosol through the filter 120 includes an inward, radial path towards the orifice 122.

In one instance, the aerosol-forming substrate may be in a single, consolidated form that is configured to maintain its shape so as to allow the aerosol-forming substrate to be placed in a unified manner within the container 130. In such an instance, the single, consolidated form of the aerosol-forming substrate may be cylindrical (so as to substantially correspond to the volume of the chamber within the capsule 100) while defining a through hole configured to be aligned with the outlet opening 114 in the end cap 110 and the orifice 122 in the filter 120.

In another instance, the aerosol-forming substrate may be in a plurality of consolidated forms configured to permit the placement of each consolidated form in an individual manner within the container 130. In such an instance, each of the plurality of consolidated forms may resemble a round tablet or disc defining a through hole configured to be aligned with the outlet opening 114 in the end cap 110 and the orifice 122 in the filter 120. Each of the plurality of consolidated forms may include the same or a different type of aerosol-forming substrate. As a result, various combinations of aerosol-forming substrates may be loaded into the container 130 to achieve the desired organoleptic appeal.

Alternatively, in lieu of or in addition to the consolidated forms discussed above, the aerosol-forming substrate may be in a loose form (e.g., particles, fibers, grounds, fragments, shreds) that does not have a set shape but rather is configured to take on the shape of the chamber within the capsule 100. In such an instance, it should be understood that the loose form of the aerosol-forming substrate generally has an average size that is larger than the diameters of the openings (e.g., inlet openings 112, outlet opening 114) in the end cap 110 and the orifice 122 in the filter 120.

As discussed herein, an aerosol-forming substrate is a material or combination of materials that may yield an aerosol. An aerosol relates to the matter generated or output by the devices disclosed, claimed, and equivalents thereof. The material may include a compound (e.g., nicotine, cannabinoid), wherein an aerosol including the compound is produced when the material is heated. The heating may be below the combustion temperature so as to produce an aerosol without involving a substantial pyrolysis of the aerosol-forming substrate or the substantial generation of combustion byproducts (if any). Thus, in an example embodiment, pyrolysis does not occur during the heating and resulting production of aerosol. In other instances, there may be some pyrolysis and combustion byproducts, but the extent may be considered relatively minor and/or merely incidental.

The aerosol-forming substrate may be a fibrous material. For instance, the fibrous material may be a botanical material. The fibrous material is configured to release a compound when heated. The compound may be a naturally occurring constituent of the fibrous material. For instance, the fibrous material may be plant material such as tobacco, and the compound released may be nicotine. The term "tobacco" includes any tobacco plant material including tobacco leaf, tobacco plug, reconstituted tobacco, compressed tobacco, shaped tobacco, or powder tobacco, and combinations thereof from one or more species of tobacco plants, such as Nicotiana rustica and Nicotiana tabacum.

In some example embodiments, the tobacco material may include material from any member of the genus Nicotiana. In addition, the tobacco material may include a blend of two or more different tobacco varieties. Examples of suitable types of tobacco materials that may be used include, but are not limited to, flue-cured tobacco, Burley tobacco, Dark tobacco, Maryland tobacco, Oriental tobacco, rare tobacco, specialty tobacco, blends thereof, and the like. The tobacco material may be provided in any suitable form, including, but not limited to, tobacco lamina, processed tobacco materials, such as volume expanded or puffed tobacco, processed tobacco stems, such as cut-rolled or cut-puffed stems, reconstituted tobacco materials, blends thereof, and the like. In some example embodiments, the tobacco material is in the form of a substantially dry tobacco mass. Furthermore, in some instances, the tobacco material may be mixed and/or combined with at least one of propylene glycol, glycerin, sub-combinations thereof, or combinations thereof.

The compound may also be a naturally occurring constituent of a medicinal plant that has a medically-accepted therapeutic effect. For instance, the medicinal plant may be a *cannabis* plant, and the compound may be a cannabinoid. Cannabinoids interact with receptors in the body to produce a wide range of effects. As a result, cannabinoids have been used for a variety of medicinal purposes (e.g., treatment of pain, nausea, epilepsy, psychiatric disorders). The fibrous material may include the leaf and/or flower material from one or more species of *cannabis* plants such as *Cannabis sativa*, *Cannabis indica*, and *Cannabis ruderalis*. In some instances, the fibrous material is a mixture of 60-80% (e.g., 70%) *Cannabis sativa* and 20-40% (e.g., 30%) *Cannabis indica*.

Examples of cannabinoids include tetrahydrocannabinolic acid (THCA), tetrahydrocannabinol (THC), cannabidiolic acid (CBDA), cannabidiol (CBD), cannabinol (CBN), cannabicyclol (CBL), cannabichromene (CBC), and cannabigerol (CBG). Tetrahydrocannabinolic acid (THCA) is a precursor of tetrahydrocannabinol (THC), while cannabidiolic acid (CBDA) is precursor of cannabidiol (CBD). Tetrahydrocannabinolic acid (THCA) and cannabidiolic acid (CBDA) may be converted to tetrahydrocannabinol (THC) and cannabidiol (CBD), respectively, via heating. In an example embodiment, heat from a heater (e.g., of the heating assembly 340 shown in FIG. 8) may cause decarboxylation so as to convert the tetrahydrocannabinolic acid (THCA) in the capsule 100 to tetrahydrocannabinol (THC), and/or to convert the cannabidiolic acid (CBDA) in the capsule 100 to cannabidiol (CBD).

In instances where both tetrahydrocannabinolic acid (THCA) and tetrahydrocannabinol (THC) are present in the capsule 100, the decarboxylation and resulting conversion will cause a decrease in tetrahydrocannabinolic acid (THCA) and an increase in tetrahydrocannabinol (THC). At least 50% (e.g., at least 87%) of the tetrahydrocannabinolic acid (THCA) may be converted to tetrahydrocannabinol (THC) during the heating of the capsule 100. Similarly, in instances where both cannabidiolic acid (CBDA) and cannabidiol (CBD) are present in the capsule 100, the decarboxylation and resulting conversion will cause a decrease in cannabidiolic acid (CBDA) and an increase in cannabidiol (CBD). At least 50% (e.g., at least 87%) of the cannabidiolic acid (CBDA) may be converted to cannabidiol (CBD) during the heating of the capsule 100.

Furthermore, the compound may be or may additionally include a non-naturally occurring additive that is subsequently introduced into the fibrous material. In one instance, the fibrous material may include at least one of cotton, polyethylene, polyester, rayon, combinations thereof, or the like (e.g., in a form of a gauze). In another instance, the fibrous material may be a cellulose material (e.g., non-tobacco and/or non-*cannabis* material). In either instance, the compound introduced may include nicotine, cannabinoids, and/or flavorants. The flavorants may be from natural sources, such as plant extracts (e.g., tobacco extract, *cannabis* extract), and/or artificial sources. In yet another instance, when the fibrous material includes tobacco and/or *cannabis*, the compound may be or may additionally include one or more flavorants (e.g., menthol, mint, vanilla). Thus, the compound within the aerosol-forming substrate may include naturally occurring constituents and/or non-naturally occurring additives. In this regard, it should be understood that existing levels of the naturally occurring constituents of the aerosol-forming substrate may be increased through supplementation. For example, the existing levels of nicotine in a quantity of tobacco may be increased through supplementation with an extract containing nicotine. Similarly, the existing levels of one or more cannabinoids in a quantity of *cannabis* may be increased through supplementation with an extract containing such cannabinoids.

Figure 6:
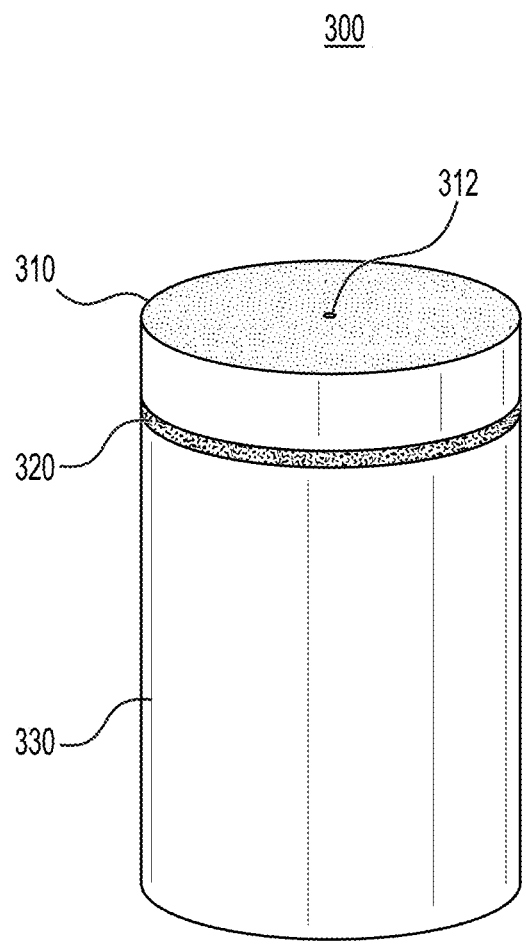
FIG. 6 is a first perspective view of an aerosol-generating device according to an example embodiment.
Figure 7:
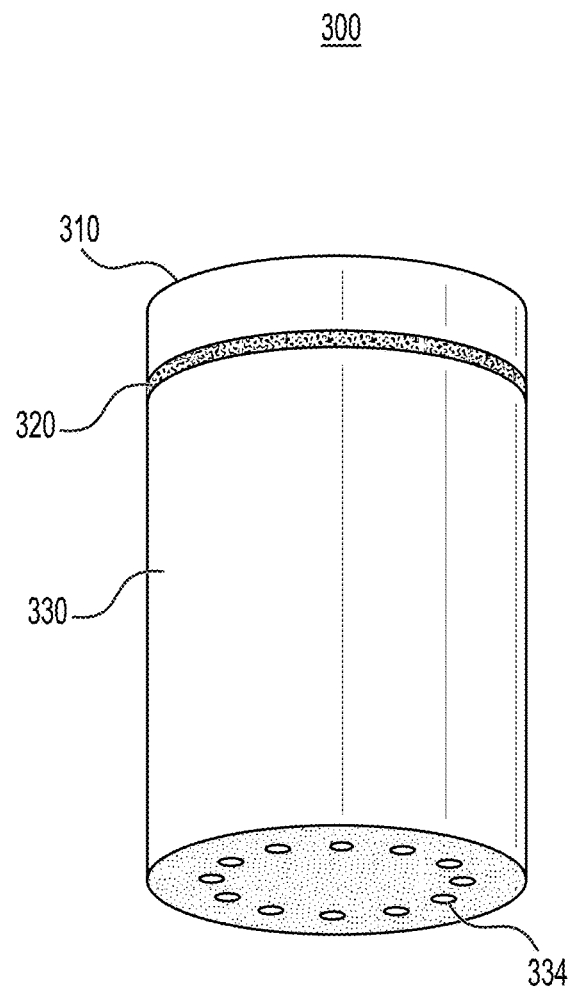
FIG. 7 is a second perspective view of the aerosol-generating device of FIG. 6.

FIG. 6 is a first perspective view of an aerosol-generating device according to an example embodiment. FIG. 7 is a second perspective view of the aerosol-generating device of FIG. 6. Referring to FIGS. 6-7, the aerosol-generating device 300 is configured to receive a capsule 200 (FIG. 8) containing an aerosol-forming substrate. As illustrated, the aerosol-generating device 300 may have a form resembling a cylinder. With such a form, the aerosol-generating device 300 may have a circular cross-section. However, it should be understood that other forms and shapes are also possible. For instance, the aerosol-generating device 300 may, in the alternative, have a form resembling a triangular prism, a cuboid, a pentagonal prism, or a hexagonal prism. With a form resembling a triangular prism, the aerosol-generating device 300 may have a triangular cross-section (e.g., shape of an equilateral triangle). With a form resembling a cuboid, the aerosol-generating device 300 may have a square cross-section or a rectangular cross-section. With a form resembling a pentagonal prism, the aerosol-generating device 300 may have a pentagonal cross-section. With a form resembling a hexagonal prism, the aerosol-generating device 300 may have a hexagonal cross-section.

As shown in the drawings, the form of the aerosol-generating device 300 may correspond to the form of the capsule 200 (e.g., cylindrical form for both the aerosol-generating device 300 and the capsule 200). However, in other instances, the form of the aerosol-generating device 300 may be different from the form of the capsule 200. For instance, the capsule 200 may have a cylindrical form, while the aerosol-generating device 300 may have one of the different forms disclosed herein (e.g., cuboid form) or vice versa.

The aerosol-generating device 300 includes a device body 330, a mouthpiece 310 configured to engage with the device body 330, and a heating assembly 340 (FIG. 8) within the device body 330. The mouthpiece 310 defines an aerosol outlet 312. The aerosol outlet 312 may be centrally disposed so as to coincide with the central longitudinal axis of the device body 330. The device body 330 may be formed of an insulating material (e.g., ceramic, metal coated with ceramic) to reduce or minimize heat loss. Additionally, the device body 330 defines a plurality of air inlets 334. The plurality of air inlets 334 may be arranged along a periphery of the upstream end face of the device body 330 (e.g., in a circular arrangement). As used herein, "upstream" (and, conversely, "downstream") is in relation to a flow of the aerosol, and "proximal" (and, conversely, "distal") is in relation to an adult operator of the device during aerosol generation.

Each of the plurality of air inlets 334 in the device body 330 may be larger than the aerosol outlet 312 in the mouthpiece 310. While twelve air inlets 334 are shown in FIG. 7, it should be understood that a different quantity may be implemented (e.g., ten air inlets, fourteen air inlets) based on the desired distribution of air flow within and through the aerosol-generating device 300. Furthermore, a gasket 320 may be disposed between the mouthpiece 310 and the device body 330. The gasket 320 may help to ensure a relatively air-tight seal such that incoming air will essentially only enter the aerosol-generating device 300 via the air inlets 334 in the device body 330.

Figure 8:
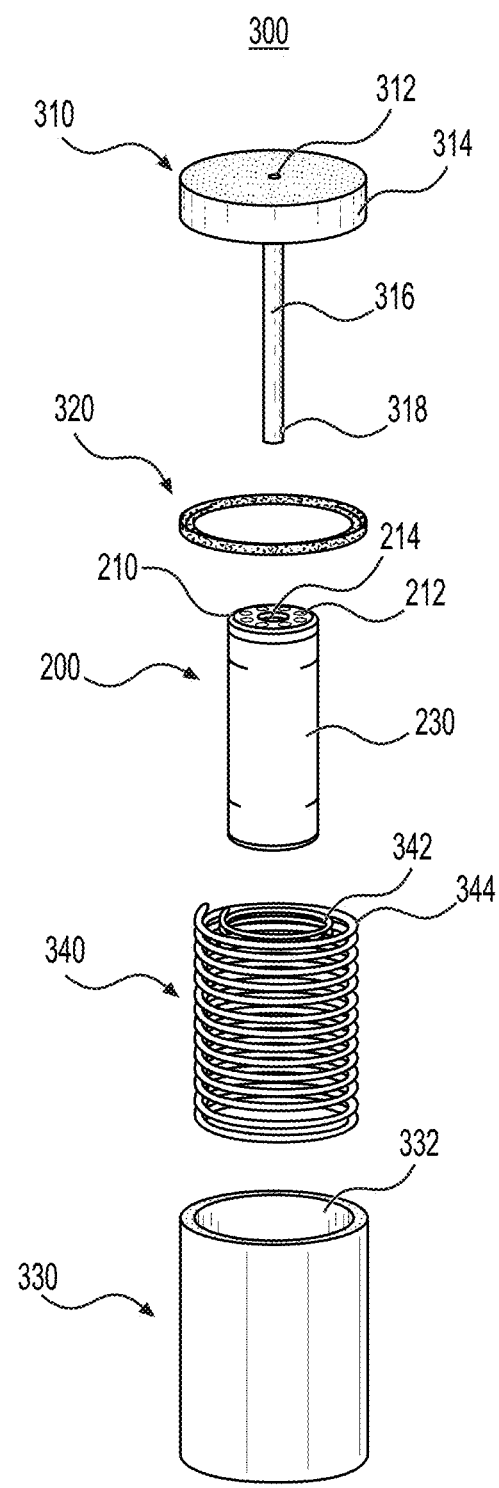
FIG. 8 is an exploded view of the aerosol-generating device of FIG. 6.
Figure 9:
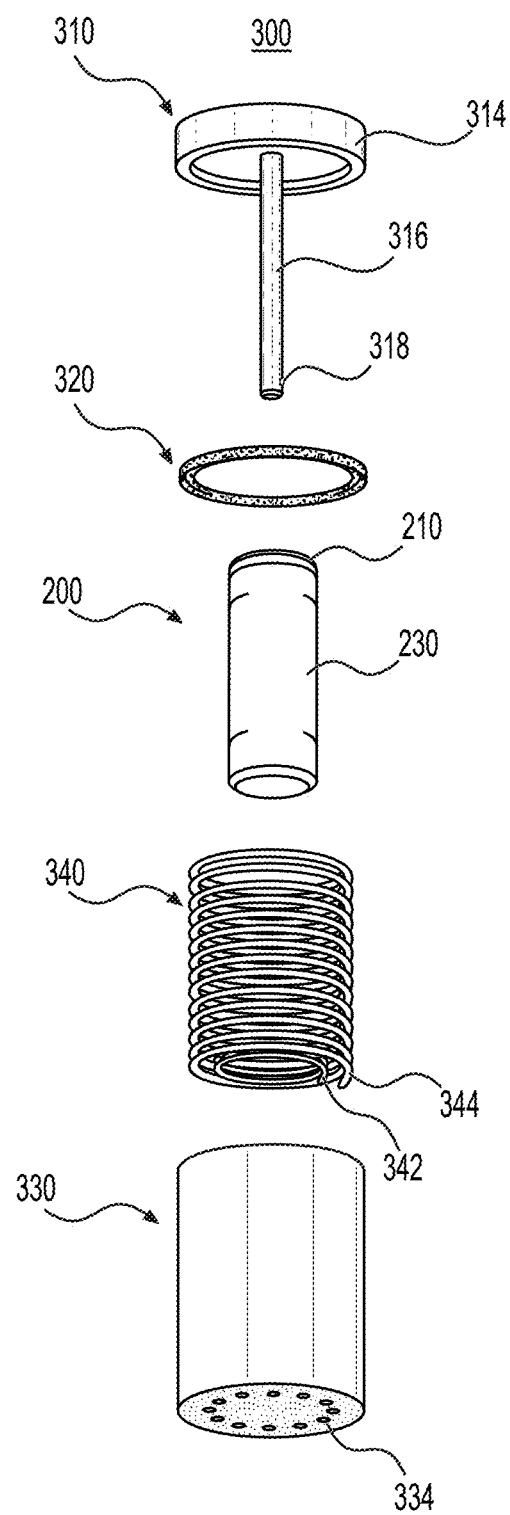
FIG. 9 is an exploded view of the aerosol-generating device of FIG. 7.
Figure 10:
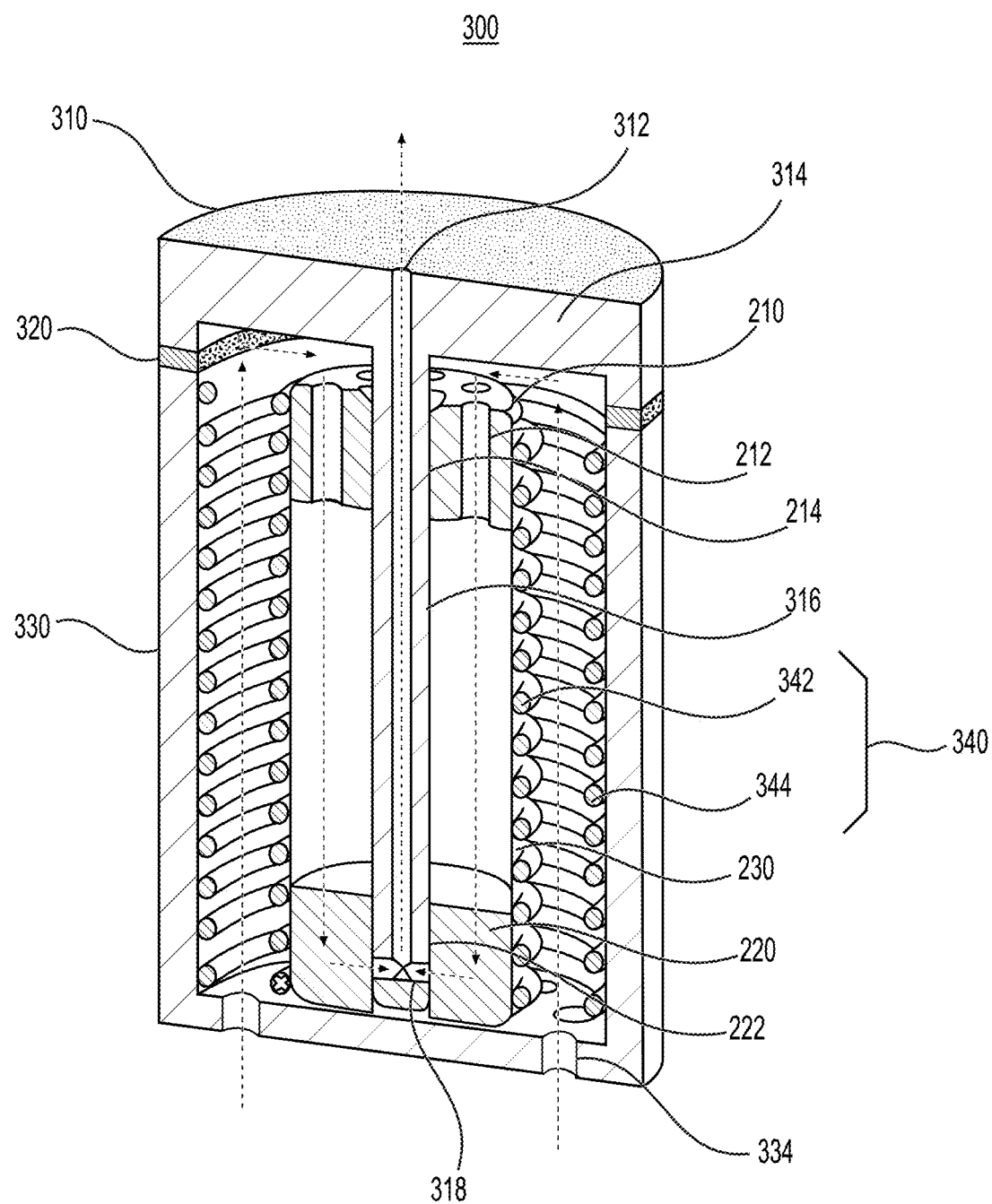
FIG. 10 is a cross-section view of the aerosol-generating device of FIG. 6.

FIG. 8 is an exploded view of the aerosol-generating device of FIG. 6. FIG. 9 is an exploded view of the aerosol-generating device of FIG. 7. Referring to FIGS. 8-9, the device body 330 defines a compartment 332 within which a heating assembly 340 is disposed. The device body 330 is configured to receive a capsule 200 within the compartment 332 such that the capsule 200 is in thermal contact with the heating assembly 340. The capsule 200 in FIGS. 8-9 may be the same as the capsule 100 in FIGS. 1-5. For instance, the end cap 210, the inlet opening 212, the outlet opening 214, the filter 220 (FIG. 10), the orifice 222 (FIG. 10), and the container 230 of the capsule 200 may be as described in connection with the end cap 110, the inlet opening 112, the outlet opening 114, the filter 120, the orifice 122, and the container 130 of the capsule 100. Although not illustrated, it should be understood that the capsule 200 may also include an aerosol-forming substrate within, which may be as described in connection with the aerosol-forming substrate of the capsule 100. As a result, the relevant disclosures above of the features in common should be understood to apply to this section and may not have been repeated in the interest of brevity.

The mouthpiece 310 includes a head portion 314 and a conduit portion 316. The conduit portion 316 defines an aperture 318 in its upstream end as well as an internal channel that fluidically connects the aperture 318 to the aerosol outlet 312. The mouthpiece 310 is configured to engage the device body 330 so as to enclose the capsule 200 and the heating assembly 340 therein. Additionally, the gasket 320 may be clamped between the mouthpiece 310 and the device body 330. In particular, the gasket 320 may have an annular form configured to be clamped between the head portion 314 of the mouthpiece 310 and the rim of the device body 330.

In an example embodiment, the capsule 200 may be regarded as a consumable part that is removed (e.g., once the aerosol-forming substrate therein is depleted or deemed expired) and replaced with a new capsule before the operation of the aerosol-generating device 300 is resumed. In this regard, the capsule 200 may also be considered disposable. On the other hand, the mouthpiece 310, the gasket 320, the heating assembly 340, and the device body 330 may be regarded as durable parts that are designed to last multiple operations of the aerosol-generating device 300 (if not the lifetime of the aerosol-generating device 300). In this regard, the mouthpiece 310, the gasket 320, the heating assembly 340, and the device body 330 may also be considered reusable.

The heating assembly 340 is configured to heat the aerosol-forming substrate within the capsule 200 via one of conduction, convection, or both conduction and convection so as to generate an aerosol. As illustrated, the heating assembly 340 may include a first heater 342 and a second heater 344. In an example embodiment, the first heater 342 and the second heater 344 are separate structures configured to permit independent operation. Alternatively, the first heater 342 and the second heater 344 may be a continuous structure configured for simultaneous operation. The first heater 342 may be primarily responsible for heating the aerosol-forming substrate within the capsule 200 via conduction, while the combination of the first heater 342 and the second heater 344 may be responsible for heating the aerosol-forming substrate within the capsule 200 via convection.

The first heater 342 may be in a form of an inner coil, while the second heater 344 may be in a form of an outer coil that surrounds the inner coil. In such an instance, the first heater 342 and the second heater 344 may be arranged concentrically so as to spiral around the central longitudinal axis of the device body 330. Additionally, the wire diameter, the pitch, the coil angle, the free length, and/or the material of construction of the first heater 342 may be the same as the wire diameter, the pitch, the coil angle, the free length, and/or the material of construction of the second heater 344, although example embodiments are not limited thereto. Furthermore, the free lengths of the first heater 342 and the second heater 344 may have magnitudes that are at least the height of the container 230 of the capsule 200 to enhance the heating the aerosol-forming substrate therein during aerosol generation. In another instance, the first heater 342 and the second heater 344 may be in the form of ceramic heaters, silicon heaters, and/or flexible polymer heaters.

With a coil configuration, the inner diameter of the first heater 342 may substantially correspond to the outer diameter of the capsule 200. As a result, the first heater 342 may physically contact (e.g., squeeze) the container 230 of the capsule 200 when the capsule 200 is received within the compartment 332 of the device body 330. Additionally, the outer diameter of the second heater 344 may substantially correspond to the inner diameter of the device body 330. As a result, the second heater 344 may contact (e.g., press against) the inner sidewall of the device body 330. Furthermore, based on the positioning of the heating assembly 340 within the compartment 332 of the device body 330, the air inlets 334 may be between first heater 342 and the second heater 344. As a result, incoming air entering the device body 330 via the air inlets 334 will flow between the first heater 342 and the second heater 344 so as to become a heated flow that enters the capsule 200 and heats the aerosol-forming substrate therein via convection.

While coil configurations have been discussed above, it should be understood that other configurations are also possible for the first heater 342 and the second heater 344. For instance, the first heater 342 and the second heater 344 may be structured as waveforms configured to encircle the capsule 200. In such an instance, the first heater 342 and the second heater 344 may alternate between extending toward the rim at the proximal end of the device body 330 and extending toward the distal end of the device body 330. In particular, the amplitudes of the waveforms of the first heater 342 and the second heater 344 may have magnitudes that are about half the height of the container 230 of the capsule 200, while the wave heights of the waveforms of the first heater 342 and the second heater 344 may have magnitudes that are about the height of the container 230 of the capsule 200 to enhance the heating the aerosol-forming substrate therein during aerosol generation.

The waveforms of the first heater 342 and the second heater 344 may resemble a compressed oscillation or zigzag and may have a plurality of parallel segments (e.g., that extend longitudinally relative to the device body 330). In particular, the waveforms may include a pulse wave (e.g., rectangular wave), a triangle wave, a sawtooth wave, or a sine wave. The waveform of the first heater 342 may be the same type as the waveform of the second heater 344, although example embodiments are not limited thereto. In instances where the capsule 200 has a non-cylindrical form (e.g., a form resembling a triangular prism, a cuboid, a pentagonal prism, or a hexagonal prism), it should be understood that the heater patterns (e.g., which may be cut from a sheet material) may be bent as needed to obtain the appropriate first and second heaters that can better accommodate (e.g., improve the thermal contact with) the capsule 200.

In an example embodiment, the first heater 342 and the second heater 344 are configured to undergo Joule heating (which is also known as ohmic/resistive heating) upon the application of an electric current thereto. Stated in more detail, the first heater 342 and the second heater 344 may be formed of one or more conductors and configured to produce heat when an electric current passes therethrough. The electric current may be supplied (e.g., independently) to the first heater 342 and the second heater 344 from a power source (e.g., battery) within the aerosol-generating device 300. Suitable conductors for the first heater 342 and the second heater 344 include an iron-based alloy (e.g., stainless steel) and/or a nickel-based alloy (e.g., nichrome). The first heater 342 and the second heater 344 may have a resistance of about 0.4-2.5 Ohms (e.g., 1.0-2.0 Ohms).

FIG. 10 is a cross-section view of the aerosol-generating device of FIG. 6. Referring to FIG. 10, to enable the operation of the aerosol-generating device 300, the capsule 200 is inserted into the compartment 332 of the device body 330 so as to be received by the first heater 342. In the event of a resilient configuration of the first heater 342 as an inner coil, the first heater 342 may physically grip the capsule 200 so as to hold the capsule 200 in a desired position while also improving the thermal contact with the container 230 of the capsule 200. When the capsule 200 is seated within the device body 330, an annular space is defined by the outer sidewall of the capsule 200 and the inner sidewall of the device body 330. As illustrated, the first heater 342 and the second heater 344 are within this annular space, wherein the first heater 342 is against the outer sidewall of the capsule 200, and the second heater 344 is against the inner sidewall of the device body 330.

Once the capsule 200 is seated, the mouthpiece 310 is configured to engage with the device body 330 to enclose the capsule 200 such that the conduit portion 316 extends through the outlet opening 214 in the end cap 210, through the aerosol-forming substrate, and into the filter 220 of the capsule 200. The conduit portion 316 of the mouthpiece 310 may have an upstream tip that is rounded to facilitate its insertion into the capsule 200. In some instances, the upstream tip of the conduit portion 316 of the mouthpiece 310 may be tapered (e.g., to a point) to further ease its insertion through the aerosol-forming substrate within the capsule 200.

As shown in FIG. 10, when the capsule 200 is enclosed within the compartment 332 of the device body 330, the gasket 320 will be clamped between the mouthpiece 310 and the device body 330. Additionally, the upstream tip of the conduit portion 316 of the mouthpiece 310 will be embedded within the orifice 222 of the filter 220. In particular, the aperture 318 in the upstream tip of the conduit portion 316 will also be covered, surrounded, or otherwise obscured by the filter 220. As a result, any flow into the aperture 318 must first pass through the filter 220. The aperture 318 may be a through hole so as to provide two entrances into the conduit portion 316 of the mouthpiece 310. In some instances, the aperture 318 may be in a form of two intersecting through holes (e.g., x configuration, cross configuration) so as to provide four entrances into the conduit portion 316 of the mouthpiece 310.

As noted supra, the gasket 320 may help to ensure a relatively air-tight seal such that incoming air will essentially only enter the aerosol-generating device 300 via the air inlets 334 in the device body 330. In one instance, the gasket 320 may be a separate component that is disposed between the mouthpiece 310 and the device body 330. In another instance, the gasket 320 may be a part of the mouthpiece 310 (e.g., adhered to the underside of the head portion 314 of the mouthpiece 310). In yet another instance, the gasket 320 may be a part of the device body 330 (e.g., adhered to the rim of the device body 330).

During the operation of the aerosol-generating device 300, incoming air (e.g., ambient air) is drawn into the device body 330 via the plurality of air inlets 334. The plurality of air inlets 334 in the upstream end of the device body 330 help to distribute the incoming air around the capsule 200. The activation of the heating assembly 340 may involve a manual operation (e.g., button-activation) and/or an automatic operation (e.g., puff-activation). Additionally, the first heater 342 and the second heater 344 of the heating assembly 340 may be activated simultaneously or sequentially. Furthermore, because the first heater 342 and the second heater 344 are configured to permit independent operation, the first heater 342 and the second heater 344 may have different heating profiles and, thus, may be at different temperatures at a given point in time.

For instance, in response to a manual operation or an automatic operation, both the first heater 342 and the second heater 344 may be activated simultaneously to begin heating. In another instance, upon an initial button-activation, the first heater 342 may begin heating the capsule 200, and upon a subsequent puff-activation, the second heater 344 (in combination with the first heater 342) may begin heating the incoming air to generate a heated airflow. In yet another instance, the sequence may be reversed such that the second heater 344 begins heating in response to an initial button-activation, and the first heater 342 begins heating in response to a subsequent puff-activation. Furthermore, in each of the above instances, the heating may include a pre-heating step (at below the target/aerosolization temperature via button-activation) involving the first heater 342 and/or the second heater 344 (to reduce the time required to reach the target/aerosolization temperature) followed by a full-heating step (at the target/aerosolization temperature via puff-activation) involving both the first heater 342 and the second heater 344. The pertinent temperature sensing may be achieved via a thermocouple or by monitoring the resistance of the first heater 342 and the second heater 344.

The incoming air entering the device body 330 via the plurality of air inlets 334 is drawn into the annular space within so as to flow (e.g., in a first longitudinal direction) between the first heater 342 and the second heater 344, which heats the incoming air into a flow of heated air. When the heated air reaches the head portion 314 of the mouthpiece 310, the direction changes to an inward path (e.g., first radial direction) toward the inlet openings 212 in the end cap 210. The heated air entering the capsule 200 via the inlet openings 212 in the end cap 210 then flows (e.g., in a second longitudinal direction) through the aerosol-forming substrate (which is between the conduit portion 316 of the mouthpiece 310 and the container 230 of the capsule 200) to entrain the volatiles released therefrom. As noted supra, as a result of the first heater 342, the aerosol-forming substrate within the capsule 200 may be heated via conduction to generate an aerosol. Additionally, as a result of both the first heater 342 and the second heater 344, the heated air entering the capsule 200 may further heat the aerosol-forming substrate via convection to enhance the aerosol generation.

Once the generated aerosol within the capsule 200 enters the filter 220, the direction changes to an inward path (e.g., second radial direction) toward the aperture 318 in the conduit portion 316 of the mouthpiece 310. As a result of passing through the filter 220, the generated aerosol becomes a filtered aerosol. The filtered aerosol exits the capsule 200 via the conduit portion 316 of the mouthpiece 310. In particular, when the aperture 318 is a through hole with two entrances, the filtered aerosol from both entrances will converge to form a combined aerosol that flows (e.g., in a third longitudinal direction) through the internal channel in the conduit portion 316 and the head portion 314, which leads to the aerosol outlet 312.

While not illustrated, it should be understood that the aerosol-generating device 300 may include additional structures/components configured to provide the desired aesthetics and/or functionalities. For instance, the aerosol-generating device 300 may include an external housing structure that is designed to be visually appealing while sized to be portable and configured to facilitate ease of handling (e.g., ergonomically-shaped for one-handed operation). Also, within the external housing structure may be provided a power source and control circuitry. The power source may include one or more batteries (e.g., rechargeable battery arrangement). The control circuitry may instruct the power source to supply an electric current to the first heater 342 and the second heater 344. The instruction to supply an electric current from the power source may be in response to a manual operation (e.g., button-activation) and/or an automatic operation (e.g., puff-activation). As a result of the electric current, the capsule 200 may be conductively and/or convectively heated by the first heater 342 and the second heater 344 to generate an aerosol. The aerosol generated within the capsule 200 may be drawn from the aerosol-generating device 300 via the aerosol outlet 312 and, optionally, an additional mouthpiece accessory.

Using the capsules and devices disclosed herein, an aerosol-forming substrate may be heated conductively and/or convectively to generate an aerosol. In an example embodiment, a method of generating an aerosol may include heating a capsule including a housing, a filter, and an aerosol-forming substrate. The housing may have a gas-permeable end and an impermeable end. The method may additionally include directing a drawn flow of air along a meandering path through the capsule. The meandering path may include an entrained flow section and a filtered flow section. The entrained flow section may be from the gas-permeable end of the housing through the aerosol-forming substrate to the filter. The filtered flow section may be from the filter to the gas-permeable end of the housing.

Further to the non-limiting embodiments set forth herein, additional details of the substrates, capsules, devices, and methods discussed herein may also be found in U.S. application Ser. No. 16/451,662, filed Jun. 25, 2019, titled "CAPSULES, HEAT-NOT-BURN (HNB) AEROSOL-GENERATING DEVICES, AND METHODS OF GENERATING AN AEROSOL," Atty. Dkt. No. 24000NV-000522-US; U.S. application Ser. No. 16/252,951, filed Jan. 21, 2019, titled "CAPSULES, HEAT-NOT-BURN (HNB) AEROSOL-GENERATING DEVICES, AND METHODS OF GENERATING AN AEROSOL," Atty. Dkt. No. 24000NV-000521-US; U.S. application Ser. No. 15/845,501, filed Dec. 18, 2017, titled "VAPORIZING DEVICES AND METHODS FOR DELIVERING A COMPOUND USING THE SAME," Atty. Dkt. No. 24000DM-000012-US; and U.S. application Ser. No. 15/559,308, filed Sep. 18, 2017, titled "VAPORIZER FOR VAPORIZING AN ACTIVE INGREDIENT," Atty. Dkt. No. 24000DM-000003-US-NP, the disclosures of each of which are incorporated herein in their entirety by reference.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. A capsule for an aerosol-generating device, comprising:
a housing having a gas-permeable end and an impermeable end, the housing including a container and an end cap, the end cap defining a plurality of openings, and the plurality of openings including an outlet opening surrounded by inlet openings;
a filter disposed within the housing so as to be adjacent to the impermeable end; and
an aerosol-forming substrate disposed within the housing so as to be between the filter and the gas-permeable end, the housing configured to facilitate a heating of the aerosol-forming substrate via one of conduction, convection, or both conduction and convection so as to generate an aerosol.

2. The capsule of claim 1, wherein the gas-permeable end of the housing is configured to retain the aerosol-forming substrate while allowing air to enter the capsule and the aerosol to exit the capsule.

3. The capsule of claim 1, wherein the container has a closed end and an open end.

4. The capsule of claim 3, wherein the end cap is disposed at the open end of the container.

5. The capsule of claim 3, wherein the end cap is the gas-permeable end of the housing, and the closed end of the container is the impermeable end.

6. The capsule of claim 1, wherein a majority of the end cap is inserted within the container.

7. The capsule of claim 1, wherein the container is made of a metal.

8. The capsule of claim 7, wherein the metal includes aluminum.

9. The capsule of claim 1, wherein each of the inlet openings is smaller than the outlet opening.

10. The capsule of claim 1, wherein a quantity and size of the inlet openings are configured to provide the capsule with a resistance to draw (RTD) between 90-110 mm Hg.

11. The capsule of claim 1, wherein the outlet opening coincides with a central longitudinal axis of the container.

12. The capsule of claim 1, wherein the filter defines an orifice aligned with the outlet opening of the end cap.

13. The capsule of claim 12, wherein the orifice in the filter is configured such that a passage of the aerosol through the filter includes a radial path towards the orifice.

14. The capsule of claim 12, wherein the orifice in the filter is a central through hole.

15. The capsule of claim 1, wherein the aerosol-forming substrate includes a plant material.

16. The capsule of claim 15, wherein the plant material includes tobacco.

17. An aerosol-generating device, comprising:
a device body defining a compartment;
the capsule of claim 1 received in the compartment;
a mouthpiece including a conduit portion, the mouthpiece configured to engage with the device body such that the conduit portion extends through the aerosol-forming-substrateand into the filterof the capsule; and
a heating assembly within the device body, the heating assembly configured to heat the aerosol-forming substrate within the capsule via one of conduction, convection, or both conduction and convection so as to generate an aerosol that exits the capsule via the conduit portion of the mouthpiece.

18. The aerosol-generating device of claim 17, wherein the aerosol-forming substrate and the filter are disposed within the capsule such that air entering the capsule passes through the aerosol-forming substrate before reaching the filter, and the aerosol passes through the filter before exiting the capsule.

19. A method of generating an aerosol, comprising:
heating a capsule including a housing, a filter, and an aerosol-forming substrate,
the housing having a gas-permeable end and an impermeable end, the housing including a container and an end cap, the end cap defining a plurality of openings, the plurality of openings including an outlet opening surrounded by inlet openings,
the filter disposed within the housing so as to be adjacent to the impermeable end, and
the aerosol-forming substrate disposed within the housing so as to be between the filter and the gas-permeable end, the housing configured to facilitate a heating of the aerosol-forming substrate via one of conduction, convection, or both conduction and convection so as to generate an aerosol; and
directing a drawn flow of air along a meandering path through the capsule, the meandering path including an entrained flow section and a filtered flow section, the entrained flow section being from the gas-permeable end of the housing through the aerosol-forming substrate to the filter, the filtered flow section being from the filter to the gas-permeable end of the housing.

* * * * *